(12) United States Patent
Pregenzer et al.

(10) Patent No.: US 6,579,225 B2
(45) Date of Patent: Jun. 17, 2003

(54) IMPLANTABLE ACTUATING MECHANISM

(76) Inventors: Bruno Pregenzer, Untermieming 45a, A-6416 Mieming (AT); Arnulf Stenzl, Hechenbergweg 16, A-6170 Zirl (AT)

( * ) Notice: Subject to any disclaimer, the term of this patent is extended or adjusted under 35 U.S.C. 154(b) by 0 days.

(21) Appl. No.: 09/935,358

(22) Filed: Aug. 22, 2001

(65) Prior Publication Data

US 2002/0049364 A1 Apr. 25, 2002

Related U.S. Application Data

(63) Continuation of application No. PCT/AT00/00001, filed on Jan. 3, 2000.

(30) Foreign Application Priority Data

Feb. 22, 1999 (AT) ............................................. 290/99

(51) Int. Cl.$^7$ ............................. A61F 2/02; A61B 17/08
(52) U.S. Cl. ........................................ 600/30; 606/157
(58) Field of Search ................. 600/16, 17.18, 600/30; 606/157; 601/106, 153; 607/1, 2, 35; 623/3; 128/886, 888, 899

(56) References Cited

U.S. PATENT DOCUMENTS

| 4,453,536 A | | 6/1984 | Abild |
| 5,152,770 A | * | 10/1992 | Bengmark et al. .......... 606/157 |
| 5,518,504 A | | 5/1996 | Polyak |
| 5,888,186 A | * | 3/1999 | Trumble et al. .............. 600/16 |

FOREIGN PATENT DOCUMENTS

| EP | 0 019 644 B1 | 9/1984 |
| EP | 0 639 355 A1 | 2/1995 |

* cited by examiner

Primary Examiner—Eric F. Winakur
Assistant Examiner—Nikita R Veniaminov
(74) Attorney, Agent, or Firm—Laurence A. Greenberg; Werner H. Stemer; Ralph E. Locher

(57) ABSTRACT

An implantable actuating mechanism for an implant that can be switched between two stable states or positions, has a supporting element and a spring-loaded actuating element that can be moved relative to the supporting element. The actuating element is guided through the supporting element and has an actuator portion, located beyond the supporting element that triggers the switching between the two stable states of the implant.

35 Claims, 6 Drawing Sheets

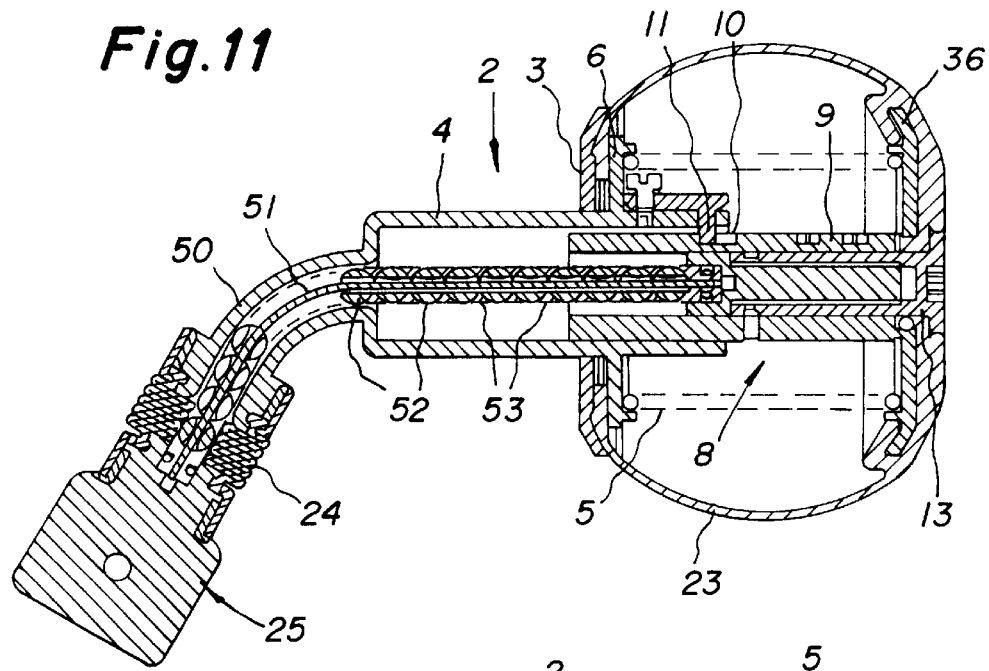
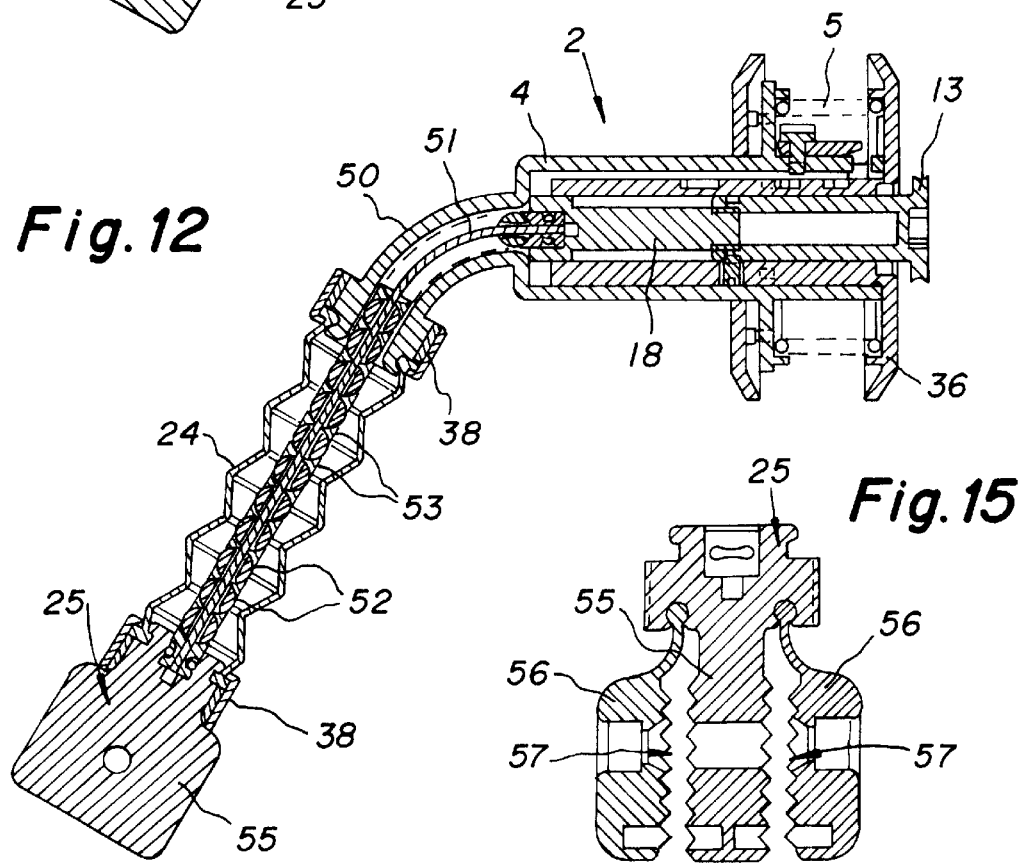

IMPLANTABLE ACTUATING MECHANISM

CROSS-REFERENCE TO RELATED APPLICATION

This application is a continuation of copending International Application No. PCT/AT00/00001, filed Jan. 3, 2000, which designated the United States.

BACKGROUND OF THE INVENTION

Field of the Invention

The invention relates to an implantable actuating mechanism for an implant which can be switched between two stable states or settings, with a support element and with a spring-activated actuating element which can be moved relative to the support element.

An actuating mechanism of this type for a closure device for natural or artificial tubular organs of the body is known, for example, from European patent application EP-A-19 644. A cuff made of a biocompatible foreign material which can be placed around the organ contains a pressure medium and cuts off the tubular organ when pressure medium is forced into the cuff from a likewise implanted pressure-medium container. The compressible pressure-medium container is provided with the actuating mechanism which on the one hand has a heart-shaped guide track and on the other hand has a pin moving therein, so that both the compressed and the relaxed positions are stable. The disadvantages associated with the prior art device lie in the use of a pressure fluid, the lines which have to be provided, the risk of leakage, and the need for an implanted storage container, etc.

To prevent urinary incontinence, European patent application EP-A-639,355 discloses a band sling which is made of a biocompatible foreign material and engages under the urethra, the ends of the band being fixed at a higher point in the body, and the central area of the band sling representing a chamber that can be filled with fluid. The amount of fluid introduced determines the height of the urethra and thus likewise can be adjusted. The European document EP 639, 355 also indicates that fascias have already been used for forming a band sling, which fascias are fixed in the body. However, subsequent correction necessitated by changes is not easily possible.

SUMMARY OF THE INVENTION

It is accordingly an object of the invention to provide an implantable actuating mechanism, which overcomes the above-mentioned disadvantages of the heretofore-known devices and methods of this general type and which mechanism, without any hydraulic system, actuates an implant that can be switched between two states or settings, and in particular prevents urinary incontinence.

With the foregoing and other objects in view there is provided, in accordance with the invention, an implantable actuating mechanism for an implant which can be switched between two stable settings, comprising:

a support element;

a spring-biased actuating element movably disposed relative to the support element, the actuating element extending through the support element and having an activation part, on a side opposite the support element, for triggering a change between the two stable settings of the implant.

In other words, the objects of the invention are attained in the actuating element is guided through the support element and, on the other side of the support element, has an activation part which triggers a switch between the two stable settings of the implant.

Depending on the intended use, the actuating mechanism is fitted at a suitable position in the body so that the actuating element can be reached through the skin and can be moved in the support element by pressure from outside. The activation part projecting inward from the support element thus executes a linear reciprocating motion which is transmitted by suitable means to the implant which is to be switched.

In accordance with a preferred embodiment of the actuating mechanism, the activation part has a holder for the two ends of a fascia. Such a holder involves in particular a combination of form closure (form lock) and frictional closure (force lock) in order to guarantee many years of stable connection. The activation part has two or three bearing plates or the like between which the fascia ends are held, elevations and corresponding depressions being provided for the form closure. The elevations can on the one hand be pyramid-shaped and have points sticking into the fascia, and on the other hand they can form cylindrical pins which engage in bores or openings. For the additional frictional closure, an undercut and resilient locking stud can also be provided which locks in one of the openings and clamps the fascia ends.

That is, the activation part has a holder for the two ends of a fascia engaging under a tubular organ. In accordance with an added feature of the invention, the holder includes a first bearing plate and a second, opposite bearing plate, and the first and second bearing plates are formed with corresponding elevations and depressions.

There is thus provided, in accordance with the invention, an implantable device for preventing urinary incontinence in a patient. The device comprises a fascia for engaging under the urethra and configured to be moved to an upper position to lift the urethral attachment, the fascia having two ends connected to the actuating mechanism as outlined above to be fixed on the pubic bone of the patient, whereby at least the upper position of the fascia is defined by one of the stable settings of the actuating element.

With the above and other objects in view there is also provided, in accordance with the invention, an implantable actuating mechanism for an implant to be switched between two stable settings, comprising:

a mounting plate to be fixed to a bone of a patient;

a support element;

a spring-activated actuating element movably disposed relative to the support element and projecting from one side through the support element to an opposite side; and an activation part on the opposite side of the support element for triggering a switch between the two stable settings of the implant, whereby the actuating mechanism is switchable between the two stable settings.

Similarly, there is provided an implantable device for preventing urinary incontinence in a patient, comprising:

a fascia configured to engage under the patient's urethra and to be moved from a lower position to an upper position for lifting a urethral attachment, the fascia having two ends;

an actuating mechanism as outlined above configured to be fixed to the patient's pubic bone;

wherein the two ends of the fascia are connected to the holder of the actuating mechanism and the upper and lower positions of the fascia are defined by the two stable settings of the actuating element.

For holding the actuating mechanism in the body, the invention provides in particular that the support element has a mounting plate for bearing or fixing on a bone.

The length of the activation element extending beyond the support element can be adjusted by means of a setscrew which can be operated at the pressure surface of the actuating element and which is accessible through the skin.

In order to achieve a better adaptation to the conditions, the activation part can be articulated on the actuating element. In another configuration, the support element can have a curved end area through which a cable line is guided which connects the activation part to the actuating part. To screen off the articulation or the cable line, a bellows is preferably provided between the support element and the activation part.

For closing and opening the urethra actively, i.e. in a way that can be influenced from outside, by lifting and lowering a fascia engaging under the urethra, which effects either a change in the vesico-urethral angle or, by lifting the urethra, clamps it off, the invention provides that the two ends of the fascia are connected to an actuating mechanism which can be fixed on the pubic bone, and both the upper closure position and the lower opening position of the fascia are in each case defined by one of the two stable settings of the actuating element.

In a further preferred embodiment of the actuating mechanism, the activation part is assigned to an electrical switching contact. The switching contact is used to close or interrupt a circuit of an implant, the energy being supplied from a current reservoir arranged in the actuating mechanism. The current reservoir can in particular be charged without contact from the outside. If, for example, striated or smooth muscle is grafted to the urethra through muscle flap transfer or as a free muscle transplant, an incorrectly functioning or nonfunctioning urethral sphincter muscle can be replaced by a muscle which is supplied with blood and, after a transition time, is reinnervated. This sphincter replacement muscle is excited to contraction by a high-frequency energy impulse transmitter, this contraction closing the urethra and preventing involuntary discharge of urine (incontinence). The impulse transmitter arranged in the body can be switched on and off by the actuating mechanism. In the switched-off state, the sphincter replacement muscle relaxes and thus permits deliberate voiding of the bladder by the patient. When the switching contact is closed directly after the bladder has been emptied, renewed contraction of the sphincter replacement muscle takes place and this allows the bladder to be filled with urine flowing from the kidneys, without inadvertent discharge of urine to the outside. This principle can also be applied to all other functions concerned with closing body openings and body passages, for example the anal sphincter, the esophageal sphincter, etc.

Other features which are considered as characteristic for the invention are set forth in the appended claims.

Although the invention is illustrated and described herein as embodied in an implantable actuating mechanism, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 11 shows a longitudinal section through a third embodiment of an actuating mechanism in a setting similar to FIG. 4;

FIG. 12 shows a longitudinal section through the third embodiment of the actuating mechanism in a setting similar to FIG. 3;

FIG. 15 shows a section through a second embodiment of a fascia holder.

DESCRIPTION OF THE PREFERRED EMBODIMENTS

Figure 6:
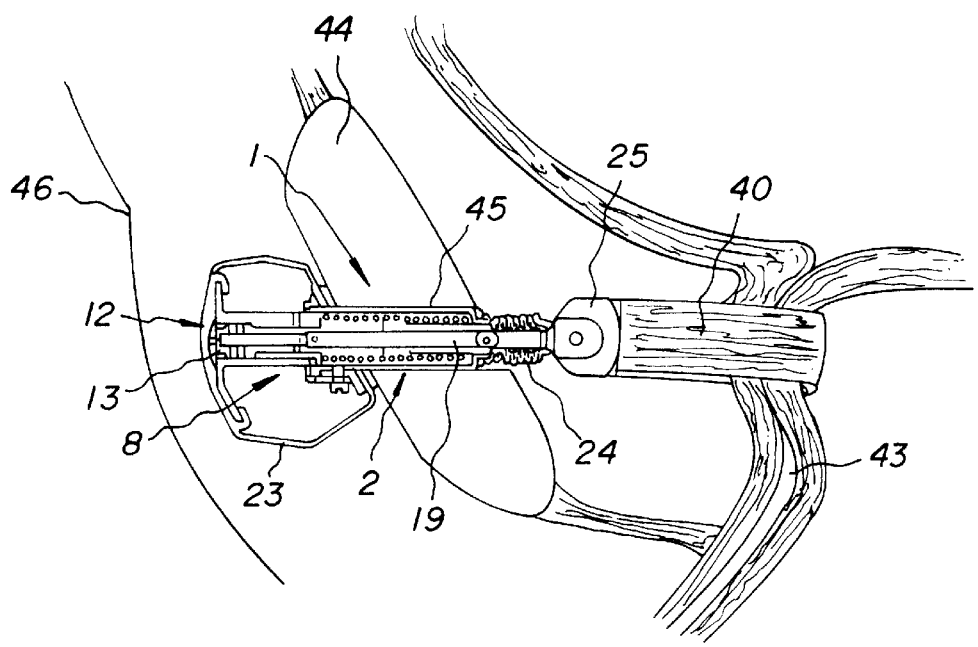
FIGS. 6 and 7 are sectional views illustrating positions of fitting on the pubic bone of a patient.
Figure 7:
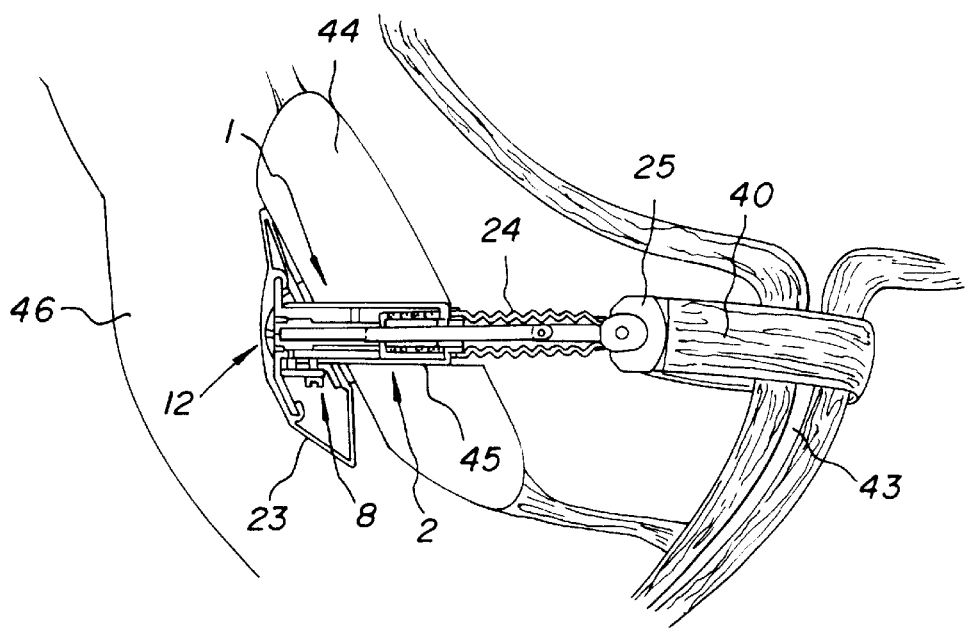
Figure 13:
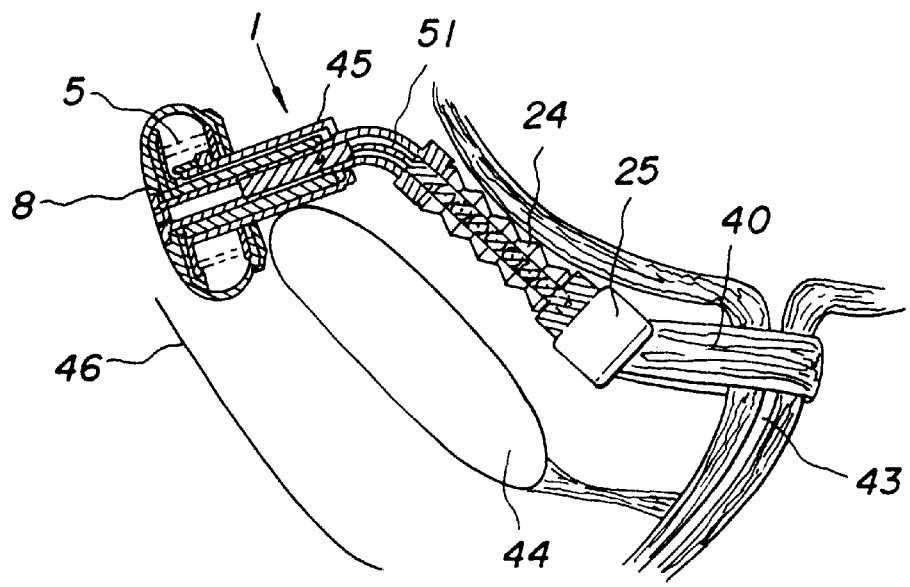
FIG. 13 shows a position of fitting of the third embodiment.

An actuating mechanism 1 according to the invention is used for switching an implant which has two stable settings (i.e., stable terminal position settings), in particular an artificial closure of a body passage, a body opening, etc, for example the urethra 43 (FIGS. 6, 7, 13). The actuating mechanism 1 can also be implanted at a suitable site and, in the case of an artificial urethral closure, is fixed to or supported on the pubic bone 44 or symphisis.

Figure 1:
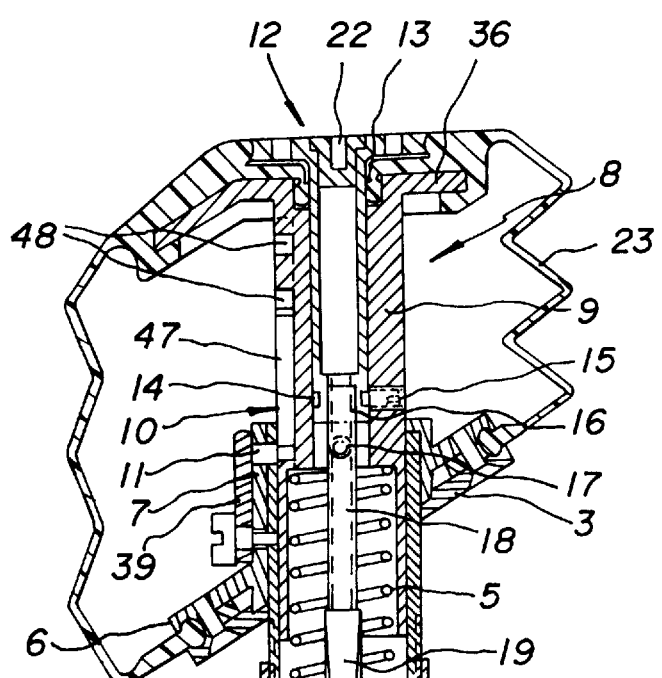
FIG. 1 is an enlarged longitudinal section through a first embodiment of an actuating mechanism according to the invention.

Referring now to the figures of the drawing in detail and first, particularly, to FIG. 1 thereof, the actuating mechanism 1 has a support element 2 which, for securing it on the pubic bone 44, has a mounting plate 3 and a guide sleeve 4 which passes through the pubic bone 44 and is surrounded by a sleeve tube 45. The mounting plate 3 is provided with lateral securing brackets, protruding perpendicular to the plane of the drawing, which can be fixed to the pubic bone with bone screws or the like.

The mounting plate 3 is also assigned a clamping plate 6, and a bellows or balloon 23 made of a physiologically compatible plastic or the like is clamped sealingly between the mounting plate 3 and the clamping plate 6, its other edge being held sealingly on a flange 36 of an actuating element 8 which is guided displaceably in the guide sleeve 4 of the support element 2.

The actuating element 8 has an inner sleeve 9 which is displaceable in the guide sleeve 4 and which is secured against twisting by two outer long grooves and two pins 17 of the guide sleeve 4 which engage in the latter, and wherein a setscrew 13 is held rotatably. The setscrew 13 is provided with an annular groove 14 wherein a guide pin 15 mounted in the sleeve 9 engages. The head of the setscrew 13 forms a press surface 12 of the actuating element and covers the edge of the bellows 23. The setscrew 13 has a slot 22 for the engagement of a tool. The setscrew 13 is hollow and in the lower area it has an internally threaded section 16 which is screwed onto a threaded rod 18. That part of the threaded rod 18 protruding from the setscrew 13 is connected to an extension rod 19 which has a square cross section and is guided secure against rotation in a square opening 20 of an insert sleeve 37 of the guide sleeve 4. If the setscrew 13 is turned using a tool engaging in the slot 22, the axial securing of the setscrew 13 by the pin 15 and the rotational securing of the extension rod 19 by the square opening 20 cause an axial displacement of the threaded rod 18 and extension rod 19, whose end protruding from the guide sleeve 4 is connected in an articulated manner to a holder 25, the function of which will be described later.

Figure 14:
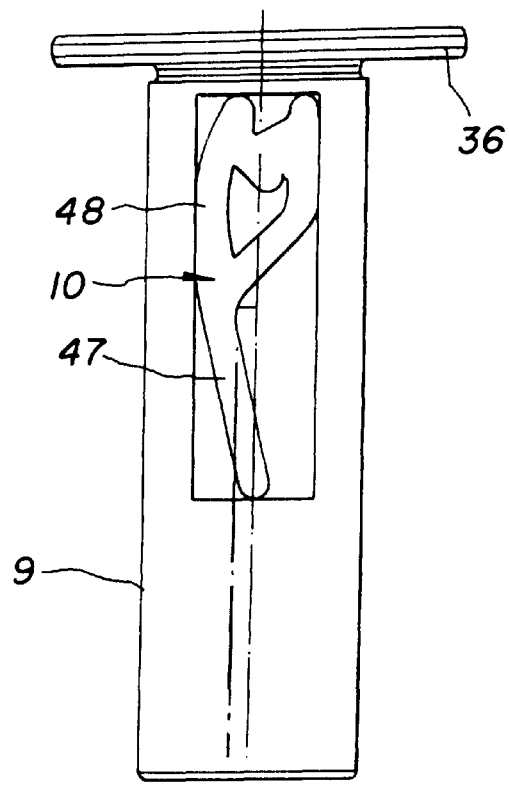
FIG. 14 shows an enlarged view of a heart-shaped guide track.

Arranged between the inner sleeve 9 and the guide sleeve 4 there is a restoring spring 5 which impacts the actuating element 8 into the setting shown in FIG. 1, wherein the actuating element 8 can be moved toward the support element 2, and the holder 25 is at its minimum distance from the guide sleeve 4. The bellows 23 is drawn out, and a second bellows 24 is strongly folded between a union nut 38 of the holder 25 and the guide sleeve 4. The clamping plate 6 has a tube piece 7 secured on the guide sleeve 4. The inner sleeve 9 of the actuating element 8 is flattened in a peripheral area and is provided there with a guide track 10 (FIG. 14) for a guide pin 11, which guide track 10 runs in a straight line and almost parallel to the axis of the actuating element 8 in a lower area 47, and, in the upper area 48, branches into an approximate heart shape. (In FIG. 1, the section of the inner sleeve 9 comprising the lower area 47 of the guide track 10 is cut away parallel to the axial plane in order to show partial areas of the guide track 10, since otherwise only short sections of the upper area 48 are visible in the axial plane. The section is plotted in FIG. 14).

The guide pin 11 is secured on a bracket 39 which is pivotable on a tube piece 7 and it protrudes through a curved slot in the tube piece 7 and the guide sleeve 4 into the guide track 10 wherein, when the actuating element 8 is actuated, i.e. when the inner sleeve 9 is displaced, it slides against the restoring spring 5. At the upper end, the approximate heart shape causes a deflection of the guide pin 11 held on the bracket 39 into its short central section, so that, when the pressure on the actuating element 8 is released, the inner sleeve 9, on account of the action of the restoring spring 15, executes only a slight return movement and remains in a second stable setting wherein the bellows 23 is strongly folded, the bellows 24 is drawn far out, and the holder pivotable about the articulation 21 at the end of the extension rod 19 is at a great distance from the end of the guide sleeve 4. The second stable setting of the actuating mechanism is defined in this position. If the actuating element is once again pressed slightly, the guide pin 11 slides on in the upper area 48 of the approximate heart shape until the second upper deflection area is reached, and from there to the lowermost starting position shown in FIG. 1 when the actuating element 8, under the action of the spring 5, is returned to the first stable setting wherein the holder 25 has again come close to the guide sleeve 4. The base of the guide track 10 can be stepped, at least in the upper area 48, at each turning point in order to ensure that the spring activated guide pin 11 does not slide to the wrong side.

Figure 2:
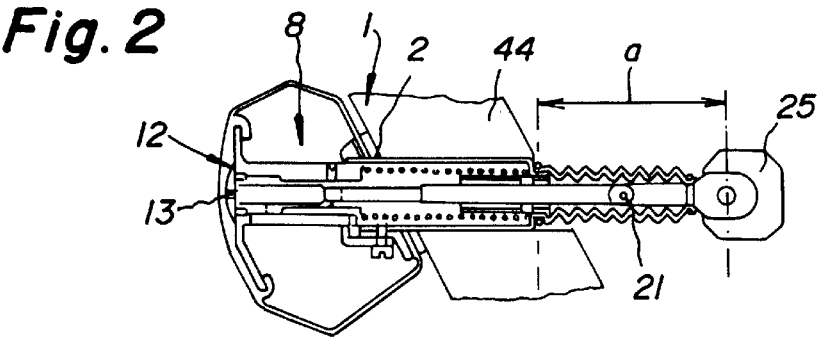
FIGS. 2 and 3 are longitudinal sections taken through the two stable settings of the actuating mechanism.
Figure 3:
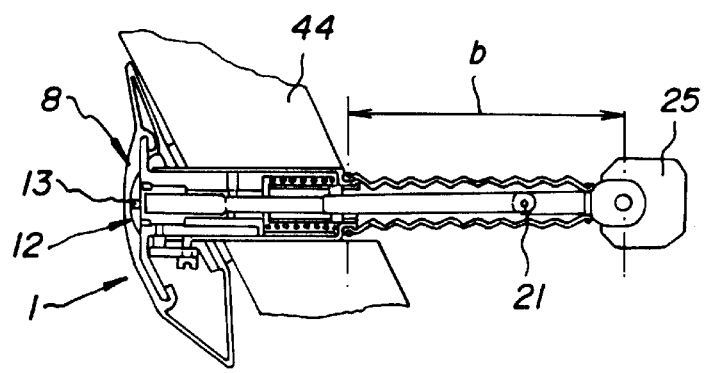

FIGS. 2 through 5 show an actuating mechanism 1 in four different positions. In FIG. 2, the actuating mechanism is in its first stable setting and the threaded rod 18 is at the outer end of the setscrew 13. The holder 25 therefore lies at a short distance a from the guide sleeve 4 of the support element 2, which in these embodiments is fixed on the outside of the pubic bone 44. When the actuating element 8 is transferred to the second stable setting shown in FIG. 3, the distance of the holder 25 from the contact sleeve 4 increases to the dimension b.

Figure 4:
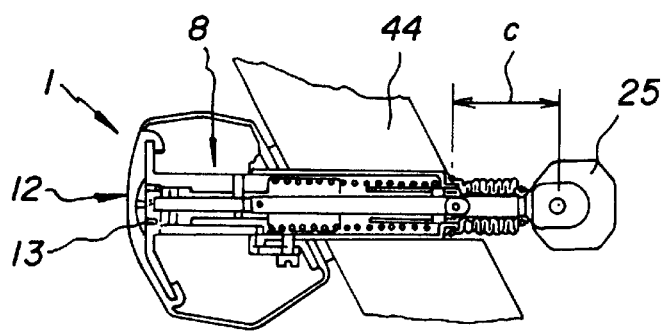
FIGS. 4 and 5 are longitudinal sections according to FIGS. 2 and 3, with a shortened activation part.
Figure 5:
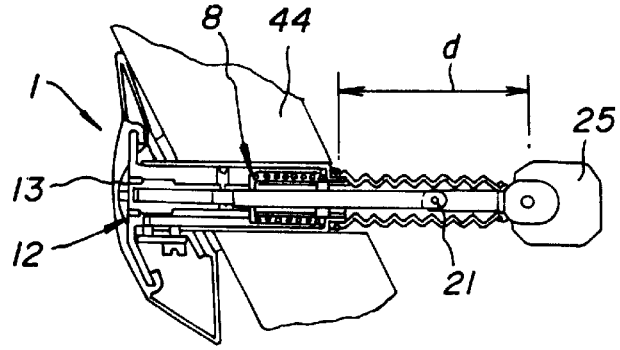

In FIG. 4, which corresponds to FIG. 1, the threaded rod 18 is drawn as far as possible into the setscrew 13, so that the distance c of the holder from the guide sleeve 4 along the entire displacement length of the actuating element 8 is smaller than the distance e in FIG. 2.

FIG. 5 once again shows the second stable setting of the actuating element 8 with the threaded rod 18 drawn in. The greatest possible distance d lies between the distances a and c in FIGS. 2 and 3.

FIGS. 6 and 7 show a preferred use of the actuating mechanism 1 for lowering a surgically raised urethral attachment, i.e. for artificial opening and closing of a urethra 43 near the urinary bladder. The artificial closure element used is a fascia 40 which is arranged under the urethra 43 and whose two ends are fixed in the holder 25 of the actuating element 8.

In the first stable setting of the implanted fascia 40 engaging under the urethra 43, the urethra, as is shown in FIG. 6, is raised and thus kinked, so that an outflow of urine is not possible. The actuating element 8 is in its first stable setting according to FIG. 2, wherein the distance a between the guide sleeve 4 and the holder 25 is defined. When the actuating element 8 is transferred to the setting shown in FIG. 3, by means of external pressure applied to the press surface 12 lying under the skin 46, the distance of the holder 25 increases to the dimension b and the fascia 40 is freed by this extent so that the urethral attachment is lowered and the urethra 43 opened. This represents the two stable settings of the implant (FIG. 7). A further external application of pressure on the press surface 12 triggers the return to the position according to FIG. 2.

If the conditions deteriorate, the actuating mechanism 1 can be readjusted by turning the setscrew 13 in a minor surgical intervention performed under local anaesthesia until the fascia 40 has been drawn back by the required dimension. The adjustment can be effected as far as the position according to FIG. 4, and the extent of the readjustment amounts to the difference of distances a and c, which can realistically amount to about 10 mm. In this adjusted position too, the urethra 43 can be opened and closed (FIGS. 4 and 5) in the manner described.

The angle between the guide sleeve 4 and the mounting plate 3 is chosen with regard to an optimum fit and is about 60°. The views shown in FIGS. 2 through 7 reveal that the articulation 21 permits a pivoting of the holder 25 about an approximately horizontal axis, so that account can be taken as far as possible of the different anatomical conditions.

Figure 8:
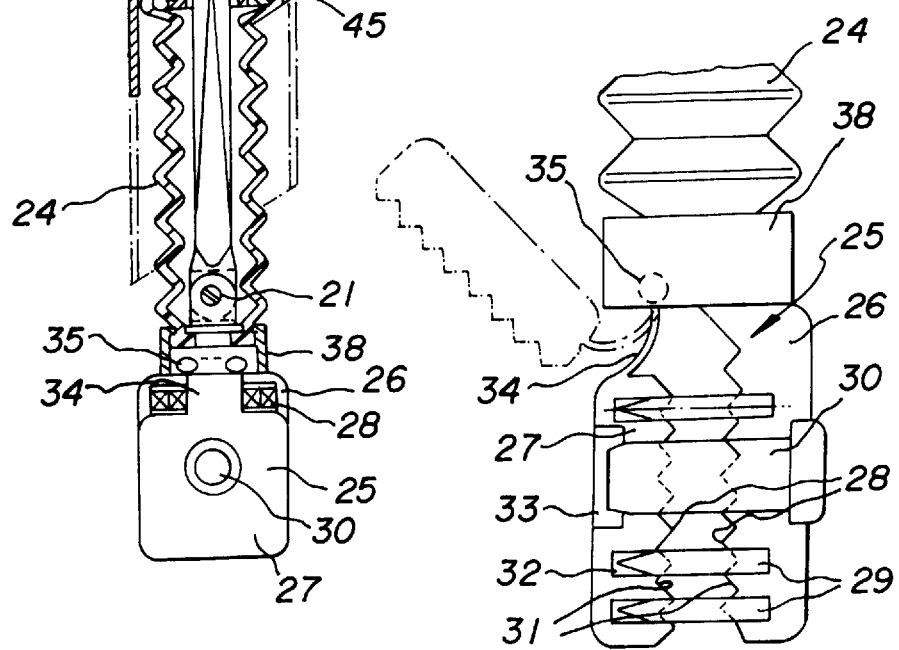
FIG. 8 is a diagrammatic side view of a fascia holder.

FIG. 8 shows an embodiment of the holder 25 in a side view. A first bearing plate 26 is connected to the actuating element 8 via the articulation 21, a second bearing plate 27 being provided at its top end. The second bearing plate 27 has a stud 35 which is inserted into a groove in the top end of the bearing plate 26 and with which it is connected via a flexible band 34. Both bearing plates 26, 27 are provided, on their surfaces facing each other, with pyramid-shaped elevations 28 and depressions 31, between which the ends of the fascia 40 are arranged. Moreover, pins 29 protrude from the first bearing plate 26 and are guided through the fascia, and their pointed ends protrude into bores 32 in the second bearing plate 27. The connection between the two bearing plates 26, 27 is in the form of an undercut locking stud 30 which locks in an opening 33 in the second bearing plate 27. Instead of the locking stud 30, a rivet or the like could also be provided. Formed at the top end of the first bearing plate 26 there is a thread onto which is screwed the union nut 38 clamping the bellows 24 on the holder 25.

As FIG. 15 shows, the holder 25 can also be designed in three parts and can have a central bearing plate 55 (FIGS. 11 and 21) coupled to the actuating element 8. Outer bearing plates 56 are articulated on both sides of the central bearing plate 55, so that each end of the fascia 40 can be inserted into a separate holder slit 57. Interlocking elevations and depressions are also preferably provided on these bearing plates.

Figure 9:
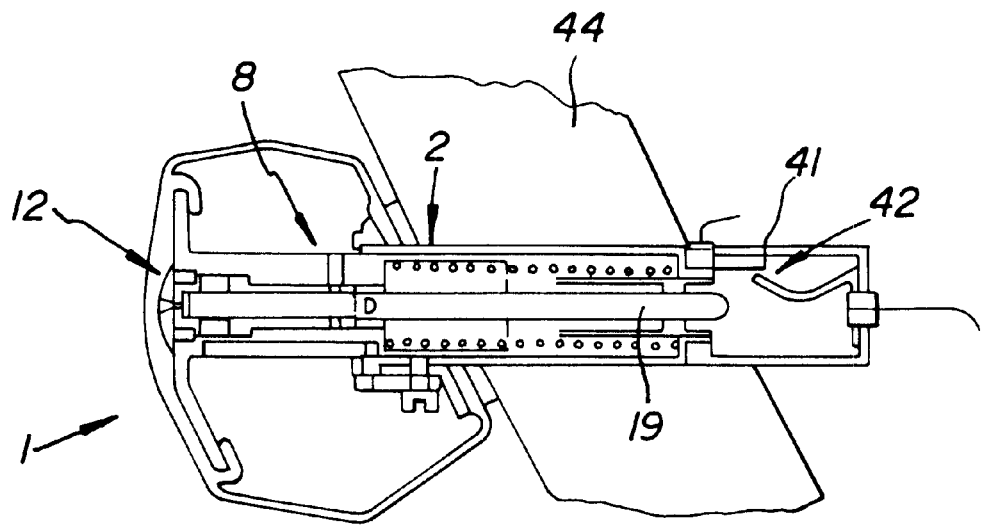
FIGS. 9 and 10 show a second embodiment of the actuating mechanism in its two stable settings.
Figure 10:
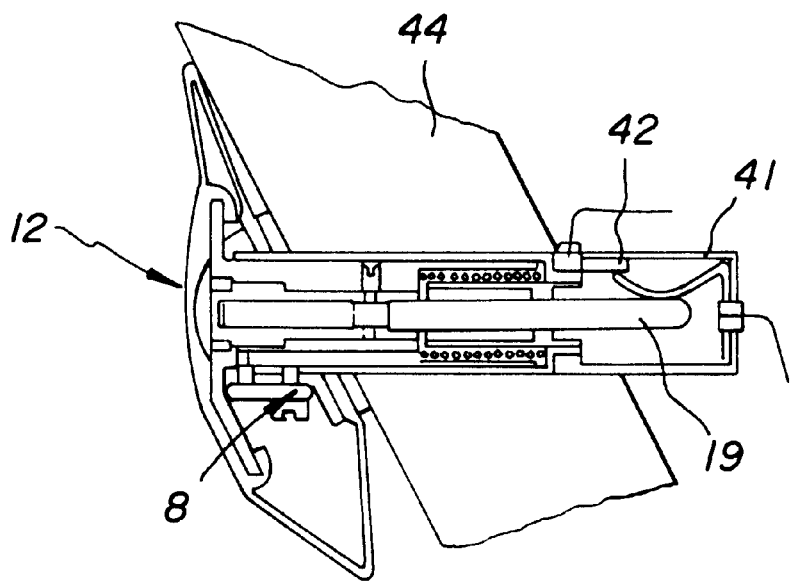

FIGS. 9 and 10 show diagrammatically an actuating mechanism 1 which is secured likewise on the pubic bone 44 or symphisis and whose actuating element 8 has an electrical switch element at the inner end. The housing placed on the guide tube 4 contains a resilient contact element 41 which is pressed by the end of the extension rod 19 toward a contact plate 42, so that a circuit is closed. The actuating mechanism can be used for example for a high-frequency impulse transmitter with which a transplanted sphincter replacement muscle or the like is stimulated.

FIGS. 11 and 12 show a third embodiment of an actuating element 8 whose support element 2 has a curved end section 50, by which means the actuating mechanism 1, as is shown in FIG. 13, can be arranged above the pubic bone. The connection between the support element 2 and the holder 25 is formed by a cable line. The cable 51 can be guided directly in the curved end section 50 or, as is shown in FIGS. 11 and 12, it can be arranged in a cable sheath if, for example, there would be too much friction between the materials used for the cable 51 and the curved end section 50. As the cable sheath must be as flexible as possible in order to slide with the cable 51 through the curved end section 50, the cable sheath 51 is preferably made up of a succession of balls 52 and intermediate disks 53 which each have two concave bearing surfaces for the balls 52. The intermediate disks 53 are thus arranged on the balls 52 with limited pivoting, and the cable line can be moved through the curved end section, as a comparison of FIGS. 11 and 12 shows. A bellows 24 is once again secured by means of a union nut 38 on the end section 50 of the support element 2 and on the holder 25, which nut is preferably provided with a restoring spring. This restoring spring provided inside the bellows 24 or in its wall acts against the restoring spring 5 provided inside the first bellows 23 but is weaker than it.

The rest of the structure of the actuating element 8 largely corresponds to the embodiment in FIG. 1. The inner sleeve 9 displaceable in the guide sleeve 4 once again has a heart-shaped guide track 10, which can be seen in FIG. 14, and wherein the transversely articulated guide pin 11 slides along and can assume two stable settings. In one stable setting the guide pin 11 lies at the lower end of the lower area 47 (FIG. 11) and in the other setting it lies in the central depression of the heart shape in the upper area 48. In contrast to FIG. 1, the longitudinal sections in FIGS. 11 and 12 lie completely in an axial plane so that only short areas of the guide track 10 are visible, FIG. 12 showing a maximally compressed setting of the actuating element 8, wherein the guide pin 11 is swiveled out laterally in the upper area 48. (For reasons of clarity, the first bellows 23 configured in a balloon shape in FIG. 11 is not shown in FIG. 12).

We claim:

1. An implantable actuating mechanism for an implant which can be switched between two stable settings, comprising:
    a support element;
    a spring-biased actuating element movably disposed relative to said support element, said actuating element extending through said support element and having an activation part, on a side opposite said support element, for triggering a change between the two stable settings of the implant, said activation part having a holder for holding two ends of a fascia engaging under a tubular organ.

2. The actuating mechanism according to claim 1, wherein said holder includes a first bearing plate and a second, opposite bearing plate, and said first and second bearing plates are formed with corresponding elevations and depressions.

3. The actuating mechanism according to claim 2, wherein said elevations include a set of elevations ending in points.

4. The actuating mechanism according to claim 2, wherein said elevations include a set of elevations formed by cylindrical pins and said depressions include bores configured to receive said pins.

5. The actuating mechanism according to claim 1, wherein said holder has a first, central bearing plate and two outer bearing plates formed with corresponding elevations and depressions.

6. The actuating mechanism according to claim 5, wherein said elevations include a set of elevations ending in points.

7. The actuating mechanism according to claim 5, wherein said elevations include a set of elevations formed by cylindrical pins and said depressions include bores configured to receive said pins.

8. The actuating mechanism according to claim 1, wherein said activation part is articulated on said actuating element.

9. The actuating mechanism according to claim 1, wherein said support element has a curved end area, and said activation part is connected to said actuating part by way of a cable guided through said curved end area.

10. The actuating mechanism according to claim 9, wherein said cable is disposed in a cable sheath having a succession of balls and intermediate disks with spherical bearing surfaces.

11. The actuating mechanism according to claim 1, which comprises a bellows between said support element and said activation part.

12. The actuating mechanism according to claim 1, wherein said actuating element includes a setscrew for adjusting a length of said activation part.

13. The actuating mechanism according to claim 1, wherein said support element includes a mounting plate for one of supporting and fixing on a bone of a patient.

14. The actuating mechanism according to claim 1, wherein said activation part is assigned to an electrical switching contact.

15. An implantable device for preventing urinary incontinence in a patient having a urethra with a urethral attachment and a pubic bone, the device comprising a fascia for engaging under the urethra and configured to be moved to an upper position to lift the urethral attachment, said fascia having two ends connected to the actuating mechanism according to claim 1 to be fixed on the pubic bone of the patient, whereby at least the upper position of said fascia is defined by one of the stable settings of the actuating element.

16. An implantable actuating mechanism for an implant to be switched between two stable settings, comprising:
    a mounting plate to be fixed to a bone of a patient;
    a support element;
    a spring-activated actuating element movably disposed relative to said support element and projecting from one side through said support element to an opposite side; and
    an activation part on the opposite side of said support element for triggering a switch between the two stable settings of the implant, whereby the actuating mechanism is switchable between the two stable settings.

17. The actuating mechanism according to claim 16, wherein said activation part is articulated on said actuating element.

18. The actuating mechanism according to claim 16, wherein said activation part has a holder for holding two ends of a fascia engaging under a tubular organ.

19. The actuating mechanism according to claim 18, wherein said holder includes a first bearing plate and a second, opposite bearing plate, and said bearing plates are formed with corresponding elevations and depressions.

20. The actuating mechanism according to claim 18, wherein said holder has a first, central bearing plate and two outer bearing plates formed with corresponding elevations and depressions.

21. The actuating mechanism according to claim 18, wherein said holder includes at least one bearing plate formed with elevations ending in points.

22. The actuating mechanism according to claim 18, wherein said holder includes two bearing plates respectively formed with elevations including a set of elevations formed by cylindrical pins and depressions including bores configured to receive said pins.

23. An implantable actuating mechanism for an implant to be switched between two stable settings, comprising:
a support element having a mounting plate for mounting on a bone of a patient and a curved end portion;
a spring-activated actuating element movably disposed relative to said support element and guided through said support element;
a cable guided through said curved end portion of said support element and connecting said actuating element to an activation part on an opposite side of said end portion, wherein said activation part triggers a switch between the two settings of the implant and wherein the actuating mechanism is switchable between two stable settings.

24. The actuating mechanism according to claim 23, wherein said activation part has a holder for holding two ends of a fascia engaging under a tubular organ.

25. The actuating mechanism according to claim 24, wherein said holder includes a first bearing plate and a second, opposite bearing plate, and said bearing plates are formed with corresponding elevations and depressions.

26. The actuating mechanism according to claim 25, wherein said holder has a first, central bearing plate and two outer bearing plates formed with corresponding elevations and depressions.

27. The actuating mechanism according to claim 24, wherein said holder includes at least one bearing plate formed with elevations ending in points.

28. The actuating mechanism according to claim 24, wherein said holder includes two bearing plates respectively formed with elevations including a set of elevations formed by cylindrical pins and depressions including bores configured to receive said pins.

29. An implantable device for preventing urinary incontinence in a patient, comprising:
a fascia configured to engage under the patient's urethra and to be moved from a lower position to an upper position for lifting a urethral attachment, said fascia having two ends;
an actuating mechanism according to claim 24 configured to be fixed to the patient's pubic bone;
wherein said two ends of said fascia are connected to said holder of said actuating mechanism and the upper and lower positions of the fascia are defined by the two stable settings of said actuating element.

30. The actuating mechanism according to claim 23, wherein said cable is disposed in a cable sheath having a succession of balls and intermediate disks with spherical bearing surfaces.

31. The actuating mechanism according to claim 23, which comprises a bellows disposed between said support element and said activation part.

32. The actuating mechanism according to claim 23, wherein said activation part is assigned to an electrical switching contact.

33. An implantable actuating mechanism for an implant which can be switched between two stable settings, comprising:
a support element;
a spring-biased actuating element movably disposed relative to said support element, said actuating element extending through said support element and having an activation part, on a side opposite said support element, for triggering a change between the two stable settings of the implant, said actuating element including a setscrew for adjusting a length of said activation part.

34. An implantable actuating mechanism for an implant which can be switched between two stable settings, comprising:
a support element;
a spring-biased actuating element movably disposed relative to said support element, said actuating element extending through said support element and having an activation part, on a side opposite said support element, for triggering a change between the two stable settings of the implant, said support element including a mounting plate for one of supporting and fixing on a bone of a patient.

35. An implantable actuating mechanism for an implant which can be switched between two stable settings, comprising:
a support element;
a spring-biased actuating element movably disposed relative to said support element, said actuating element extending through said support element and having an activation part, on a side opposite said support element, for triggering a change between the two stable settings of the implant, wherein said activation part is assigned to an electrical switching contact.

* * * * *